United States Patent
Douce et al.

(10) Patent No.: US 10,141,172 B2
(45) Date of Patent: Nov. 27, 2018

(54) SYNCHRONISED VARIATION OF SOURCE CONDITIONS OF AN ATMOSPHERIC PRESSURE CHEMICAL IONISATION MASS SPECTROMETER COUPLED TO A GAS CHROMATOGRAPH TO IMPROVE STABILITY DURING ANALYSIS

(71) Applicant: Micromass UK Limited, Wilmslow (GB)

(72) Inventors: David Douce, Congleton (GB); Gareth Rhys Jones, Altrincham (GB)

(73) Assignee: MICROMASS UK LIMITED, Wilmslow (GB)

( * ) Notice: Subject to any disclaimer, the term of this patent is extended or adjusted under 35 U.S.C. 154(b) by 56 days.

(21) Appl. No.: 15/128,293

(22) PCT Filed: Mar. 27, 2015

(86) PCT No.: PCT/GB2015/050942
§ 371 (c)(1),
(2) Date: Sep. 22, 2016

(87) PCT Pub. No.: WO2015/145176
PCT Pub. Date: Oct. 1, 2015

(65) Prior Publication Data
US 2017/0110310 A1 Apr. 20, 2017

(30) Foreign Application Priority Data

Mar. 28, 2014 (EP) ..................................... 14162448
Mar. 28, 2014 (GB) .................................. 1405625.3

(51) Int. Cl.
*H01J 49/00* (2006.01)
*G01N 30/72* (2006.01)
(Continued)

(52) U.S. Cl.
CPC ........ *H01J 49/168* (2013.01); *G01N 30/7206* (2013.01); *H01J 49/0031* (2013.01); *H01J 49/145* (2013.01)

(58) Field of Classification Search
None
See application file for complete search history.

(56) References Cited

U.S. PATENT DOCUMENTS 4,808,820 A 2/1989 Blau
5,012,052 A 4/1991 Hayes
(Continued)

FOREIGN PATENT DOCUMENTS

JP 2002329475 11/2002

OTHER PUBLICATIONS

Anonymous, "APGC", Aug. 2013, pp. 1-5, Retrieved from Internet on May 8, 2015, URL:http//www.waters.com/webassets/cms/library/docs/720004771EN_final.pdf.
(Continued)

*Primary Examiner* — Jason McCormack
*Assistant Examiner* — James Choi
(74) *Attorney, Agent, or Firm* — Womble Bond Dickinson (US) LLP; Deborah M. Vernon; Heath T. Misley

(57) ABSTRACT

A mass spectrometer is disclosed comprising a gas chromatography separation device, an atmospheric pressure ionization ion source and a control system arranged and adapted: (i) to operate the atmospheric pressure ionization ion source at one or more first settings for a first period of time while one or more solvents elute from the gas chromatography separation device during a solvent front; and then (ii) to operate the atmospheric pressure ionization ion source at one or more second different settings for a second subsequent period of time while one or more analytes elute from the gas chromatography separation device.

18 Claims, 10 Drawing Sheets

(51) Int. Cl.
*H01J 49/16* (2006.01)
*H01J 49/14* (2006.01)

(56) References Cited

U.S. PATENT DOCUMENTS

| | | | |
|---|---|---|---|
| 7,041,972 B2 | 5/2006 | Bajic et al. | |
| 7,420,180 B2 | 9/2008 | Yamada et al. | |
| 7,642,510 B2 | 1/2010 | McEwen | |
| 8,227,764 B2 | 7/2012 | Mannino et al. | |
| 2005/0035286 A1* | 2/2005 | Bajic | H01J 49/168 250/288 |
| 2006/0186028 A1* | 8/2006 | Hughes | G01N 30/10 210/198.2 |
| 2007/0205361 A1* | 9/2007 | Russ, IV | H01J 49/0009 250/288 |
| 2010/0019142 A1* | 1/2010 | Mannino | H01J 49/147 250/282 |
| 2011/0266433 A1* | 11/2011 | Jarrell | G01N 30/7206 250/282 |
| 2012/0104246 A1* | 5/2012 | Newton | H01J 49/0431 250/288 |
| 2014/0284472 A1* | 9/2014 | Verenchikov | G01N 27/622 250/282 |
| 2014/0370613 A1 | 12/2014 | Stevens | |
| 2015/0144781 A1 | 5/2015 | Howes et al. | |
| 2015/0233866 A1* | 8/2015 | Verenchikov | G01N 27/622 250/282 |

OTHER PUBLICATIONS

Anonymous, "Filament Selection Guide for Agilent GC/MSDs", Nov. 15, 2007, pp. 1-3, Retrieved from Internet on May 26, 2015, URL:http://www.chem.agilent.com/Library/Support/Documents/F05003.pdf.

Anonymous, "Maintaining Your GC/MS System—Operate your Agilent GC/MS System with Maximum Efficiency", Jan. 1, 2001, pp. 1-48, Retrieved from Internet on May 28, 2015, URL:http://www.sisweb.com/art/pdf/ms-maint.pdf.

Anonymous, "Running a sample & Component Identification", Oct. 23, 2013, pp. 1-32, Retrieved from Internet on May 26, 2015, URL:http://qub.ac.uk/schools/SchoolofChemistryandChemicalEngineering/FileStore/InternalForms/ASEPAnalyticalServicesandEnvironmentalProjects/GCMS/Fileotupload,404680,en.pdf.

Jones et al., "Methods for Improving the Reproducibility of an Atmospheric Pressure Chemical Ionisation Source for Gas Chromatography Analysis", Jun. 17, 2014, ASMA Conference 2014, Baltimore MD, Retrieved from Internet on May 26, 2015, URL:http://www.waters.com/webassets/cms/library/docs/2014asms_jones_apgc.pdf.

Karty, "Analyzing Semi-Volatiles by GC-MS", Jul. 31, 2008, pp. 1-20, Retrieved from Internet on Aug. 13, 2014, URL:http://msf.chem.indiana.edu/docs/analyzing semi-volitalies%20by%20GC-MS%20july2008.pdf.

International Search Report and Written Opinion dated May 28, 2015 and dated Jun. 5, 2016 for International Patent Application No. PCT/GB2015/050942 (14 pages).

Anonymous "Chromatography Forum: LC-MS & GC-MS Archives: GC-MS Overload" [online]. [retrieved from the Internet: Aug. 7, 2003]. Retrieved from the Internet <URL: http://www.lcresources.com/discus/messages/5135/3713.html?WednesdayJune220040227am>.

Anonymous: "Waters Micromass Q-Tof Premier Mass Spectrometer Operator's Guide 71500089402 / Revision B" [online]. [retrieved from the Internet: Jan. 1, 2005] Retrieved from the internet <URL: http://old.vtpup.cz/common/manual/PrF_kach_Waters_Q-TOF_manual_EN.pdf>.

* cited by examiner

SYNCHRONISED VARIATION OF SOURCE CONDITIONS OF AN ATMOSPHERIC PRESSURE CHEMICAL IONISATION MASS SPECTROMETER COUPLED TO A GAS CHROMATOGRAPH TO IMPROVE STABILITY DURING ANALYSIS

CROSS-REFERENCE TO RELATED APPLICATIONS

This application is the National Stage of International Application No. PCT/GB2015/050942, filed 27 Mar. 2015 which claims priority from and the benefit of United Kingdom patent application No. 1405625.3 filed on 28 Mar. 2014 and European patent application No. 14162448.6 filed on 28 Mar. 2014. The entire contents of these applications are incorporated herein by reference.

FIELD OF THE INVENTION

The present invention relates generally to mass spectrometry and in particular to mass spectrometers and methods of mass spectrometry.

BACKGROUND

During gas chromatography analysis the elution of analytes of interest is preceded by the elution of vaporised solvent (typically 1 µL) in which the sample was contained. Under typical conditions the solvent will start to elute from the gas chromatography column within the first half a minute of the acquisition and will typically continue to elute for around two minutes.

The solvent front can have a detrimental effect on the stability and reproducibility of the ionisation of subsequent analytes when a gas chromatograph is coupled to an atmospheric pressure corona discharge ionisation source.

An atmospheric pressure corona discharge ionisation source operating in a positive ionisation mode under optimal conditions operates with a coronal form know as a "glow discharge corona". This type of corona is characterised by a steady current with little or no noise or sparking.

The mechanism for the establishment and sustainment of this corona form under the conditions under which this source operates is as follows. An electron in close proximity to the corona pin tip is accelerated towards the pin due to the high positive potential applied. If the field gradient is sufficiently high then the electron can gain enough energy between collisions with the gas about the corona pin to cause the ionisation of molecules it collides with. This ionisation event will result in a radical cation of the gas molecule and the release of an additional electron. As this ionisation event has occurred within a high field gradient it is probable that the two electrons will gain sufficient energy in their subsequent acceleration towards the corona pin to cause further ionisation. In this fashion a so-called "electron avalanche" is formed. Some of these electrons will undergo recombination reactions with the radical cations of the gas molecules, resulting in the release of a high energy photon. These photons can escape the high potential in the proximity of the tip of the corona pin and subsequently cause ionisation and the release of more electrons further out in the electric field. These electrons are then accelerated towards the pin and initiate further electron avalanches. In this fashion, once a corona has been established it can typically sustain itself.

When using a corona pin in current regulation mode (where the voltage is varied to maintain a requested current), the voltage applied to the pin is seen to increase significantly in the presence of the solvent. Once the solvent front has passed, the voltage applied to the pin in order to maintain the required corona current can vary significantly from one acquisition to the next with the result that a corresponding variation in analyte response is observed.

US 2007/0181801 (Yamada) discloses a mass spectrometer capable of switching between two different ion sources in a single experimental run. In US 2007/0181801 (Yamada), a sample is added to the upstream of a gas chromatography ("GC") column, and an atmospheric pressure chemical ionisation ("APCI") mass spectrum is obtained for an analyte elution peak. If a measured peak corresponds to an unknown ingredient of the sample (e.g. based on a known database), then the APCI ion source is switched OFF and instead an electron ionisation ("EI") ion source is used in order to obtain an EI spectrum for a peak of the unknown ingredient.

US 2005/0035286 (Micromass) discloses a mass spectrometer having an APCI ion source connected with a GC separation device. The current applied to a corona needle is repeatedly varied between two or more settings during a single experimental run in order to ionise a mixture containing both low and highly polar analytes.

WO 2014/021960 (Verenchikov) discloses a GC separator combined with an ion source, such as a chemical ionization (CI) source. The ion source has the capability to switch between ionization polarity by reverting the potential on ionizing corona discharge.

The problems inherent with coupling a gas chromatograph to an atmospheric pressure chemical ionisation ion source and operating the ion source in a conventional manner will be described with reference to FIGS. 1-3.

FIG. 1 shows an example chromatogram (total ion current "TIC") acquired on an Atmospheric Pressure Chemical Ionisation ("APCI") mass spectrometer coupled to a Gas Chromatograph ("GC"). The solvent front can be seen as a significant rise in the total ion current between 0.7 and 1.5 minutes from the start of the analysis.

Throughout the entire analysis the corona pin was set to regulate at 2.0 µA with the voltage applied to the corona pin being adjusted in order to achieve this.

FIG. 2 shows the voltage that was applied to the corona pin in order to maintain or regulate the corona current at 2.0 µA for seven successive acquisitions under the same conditions.

The influence of the solvent front on the voltage which has to be applied to the corona pin in order to maintain the corona current steady at 2.0 µA can clearly be seen in the data shown in FIG. 2.

It is apparent from FIG. 2 that the voltage applied to the corona pin rises as the vaporised solvent is introduced within the ionisation region around the tip of the corona pin and disrupts the corona discharge process. As the solvent vapour is gradually depleted the voltage is seen to drop towards the value at which it was regulating before the solvent front. However, the exact value of the corona pin voltage at any time during the acquisition is markedly different from one acquisition to the next.

FIG. 3 demonstrates how the variation in corona pin voltage can adversely influence the analyte response of 4-bromophenyl phenyl ether and shows how the response across seven sequential acquisitions was highly variable.

The analyte shown in FIG. 3, namely 4-bromophenyl phenyl ether, elutes from the gas chromatograph at an acquisition time of 6.54 mins. FIG. 3 shows the peak response for the seven successive acquisitions for which corona voltage data is shown in FIG. 2.

The corona voltage at the elution time (6.54 mins) of this particular analyte is also plotted in FIG. 3 using the secondary axis. There is a clear inverse correlation between the corona voltage and the analyte response.

It is desired to provide an improved mass spectrometer.

SUMMARY

According to an aspect there is provided a mass spectrometer comprising:

a gas chromatography separation device;

an atmospheric pressure ionisation ion source; and a control system arranged and adapted:

(i) to operate the atmospheric pressure ionisation ion source at one or more first settings for a first period of time whilst one or more solvents elute from the gas chromatography separation device during a solvent front; and then (ii) to operate the atmospheric pressure ionisation ion source at one or more second different settings for a second subsequent period of time whilst one or more analytes elute from the gas chromatography separation device.

During routine gas chromatography analysis, the elution of analytes from the gas chromatography column is preceded by the elution of vaporised solvent in which the analytes were contained and this effect is commonly referred to as a solvent front. The solvent front can disrupt the ion source ionisation conditions of the mass spectrometer and lead to significant differences in analyte response from one analysis to the next.

The embodiment results in improved reproducibility by the adjustment of various ion source conditions during the elution of the solvent.

The approach according to an embodiment is particularly advantageous in that the embodiment significantly improves the reproducibility of the detection of analytes of interest. This has various benefits including improved quantitative precision and more reliable analysis.

The methods according to an embodiment are also particularly useful for the analysis of samples which are contained within solvents such as toluene and which are known to have disruptive effects on the ionisation conditions of the ion source.

In this regard, it will be appreciated that the embodiment is distinct from the arrangements described in US 2007/0181801 (Yamada), US 2005/0035286 (Micromass) and WO 2014/021960 (Verenchikov). These arrangements merely relate to ion sources which each capable of ionizing analytes in two different modes of operation. In contrast to the various embodiments described in the present application, these arrangements are not concerned with (and do not disclose) operating an ion source at one or more first settings (that are different to one or more second settings) whilst one or more solvents elute from a gas chromatography separation device during a solvent front.

The gas chromatography separation device may comprise a gas chromatography column.

The atmospheric pressure ionisation ion source may comprise an Atmospheric Pressure Chemical Ionisation ("APCI") ionisation source.

The Atmospheric Pressure Chemical Ionisation ("APCI") ionisation source may comprise a corona discharge device for ionising analyte.

The one or more solvents elute from the gas chromatography device prior to the elution of one or more analytes from the gas chromatography device.

The one or more first settings and/or the one or more second settings may be selected from the group consisting of: (i) a current or a corona current supplied to the atmospheric pressure ionisation ion source; (ii) a gas flow or a cone gas flow; (iii) an auxiliary gas flow; (iv) a voltage or a corona voltage applied to the atmospheric pressure ionisation ion source; (v) a polarity or a corona polarity of a voltage applied to the atmospheric pressure ionisation ion source; (vi) a temperature of one or more components of the atmospheric pressure ionisation ion source; (vii) a voltage offset, an ion source voltage offset or a cone voltage offset; and (viii) a makeup gas flow, a reference gas flow or a modifier gas flow.

The Applicants have recognised that, where the APCI ionisation source comprises a corona discharge device, it is advantageous to operate the corona discharge device to produce particular types of corona (of the several distinct corona types that the device is capable of producing) during a solvent front.

The Applicants have also recognised that different types of corona are achieved by, for example, setting the APCI ionisation source to maintain a specific corona current. Thus, according to an embodiment, the control system is arranged and adapted to set the current or corona current at a first constant current value I1 during the first period of time and/or the control system is arranged and adapted to set the current or corona current at a second constant current value I2 during the second period of time.

(It will be appreciated that setting the corona current to a constant current value during a period of time may (and preferably does) involve varying the voltage applied to the corona pin to maintain the constant current value. The relationship between the current produced by a corona pin and the voltage that is applied to the pin can be characterised by an equation of the form:

$$I = kV(V - V_0),$$

where I is the current, V is voltage applied, k is a constant and $V_0$ is an onset potential.)

The control system is arranged and adapted to set the first current value I1 and/or wherein the control system is arranged and adapted to set the second current value I2 at a value selected from the group consisting of: (i) about 0 µA; (ii) about <1 µA; (iii) about 1-2 µA; (iv) about 2-3 µA; (v) about 3-4 µA; (vi) about 4-5 µA; (vii) about 5-6 µA; (viii) about 6-7 µA; (ix) about 7-8 µA; (x) about 8-9 µA; (xi) about 9-10 µA; (xii) about 10-11 µA; (xiii) about 11-12 µA; (xiv) about 12-13 µA; (xv) about 13-14 µA; (xvi) about 14-15 µA; (xvii) about 15-16 µA; (xviii) about 16-17 µA; (xix) about 17-18 µA; (xx) about 18-19 µA; (xxi) about 19-20 µA; (xxii) about 20-21 µA; (xxiii) about 21-22 µA; (xxiv) about 22-23 µA; (xxv) about 23-24 µA; (xxvi) about 24-25 µA; (xxvii) about 25-26 µA; (xxviii) about 26-27 µA; (xxix) about 27-28 µA; (xxx) about 28-29 µA; (xxxi) about 29-30 µA; (xxxii) about 30-40 µA; (xxxiii) about 40-50 µA; and (xxxiv) about >50 µA.

According to an embodiment either I1<I2 or I1>I2.

According to an embodiment, the first constant current value I1 is set at or about 0 µA. In such an arrangement, the voltage applied to the pin is preferably equal to the onset potential and the pin will operate in a coronal mode known as a "burst corona", where electron avalanches briefly form but are not sustained. The Applicants have found that this is one of the coronal modes in which it is advantageous to operate the APCI ion source during the elution of a solvent front.

According to an embodiment, the first constant current value I1 is substantially different to the second constant current value I2. The first constant current value I1 may be substantially greater than the second constant current value I2. In a particularly embodiment, the first constant current value I1 may be ten times as great as the second constant current value I2.

Where the first constant current value I1 is set to an adversely high value, such as 20 μA, the corona can be forced into another coronal form, known as a "streamer corona". Under these conditions, highly localised concentrations of charge can form their own, very steep, electric fields which themselves act as if they were the tip of the corona pin. These concentrations of charge can migrate away from the corona pin and extend the ionisation region as they migrate. These so-called streamers are extinguished before they reach as far as the nearest grounded surface; if the corona pin voltage were higher still these streamers can reach ground and a sparking event occurs.

The Applicants have found that it is advantageous to operate the corona pin in a streamer corona form during the elution of the solvent front. Thus, according to an embodiment, the first constant current value I1 is set at or about 20 μA. In other words, the Atmospheric Pressure Chemical Ionisation ion source can be (and in some embodiments is) set to operate in a streamer corona mode.

The control system is preferably arranged and adapted to vary the current or corona current as a function of time during the first period of time and/or the control system is arranged and adapted to vary the current or corona current as a function of time during the second period of time.

From the above, it will be appreciated that in some embodiments, the atmospheric pressure ionisation ion source is not turned OFF during elution of the one or more solvents from the gas chromatography separation device during a solvent front.

For example, when the corona current is set at or about 0 μA (i.e. V=$V_o$) during a solvent front, the atmospheric pressure ionisation ion source is not turned OFF. Instead, as discussed above, the atmospheric pressure ionisation ion source is in fact operating in a coronal mode known as a burst corona mode. It will further be appreciated that operating the atmospheric pressure ionisation ion source at one or more first settings is not the same as turning OFF (e.g. the filament used to produce the electrons in) a, e.g. high vacuum, electron impact (EI) or chemical ionisation (CI) source.

The control system may be arranged and adapted to set the gas flow, cone gas flow, auxiliary gas flow, makeup gas flow, reference gas flow or modifier gas flow at a first constant gas flow value Q1 during the first period of time and/or the control system may be arranged and adapted to set the gas flow, cone gas flow, auxiliary gas flow, makeup gas flow, reference gas flow or modifier gas flow at a second constant gas flow value Q2 during the second period of time.

The control system may be arranged and adapted to set the first gas flow value Q1 and/or the control system may be arranged and adapted to set the second gas flow value Q2 at a value selected from the group consisting of: (i) about 0 L/Hr; (ii) about <10 L/Hr; (iii) about 10-20 L/Hr; (iv) about 20-30 L/Hr; (v) about 30-40 L/Hr; (vi) about 40-50 L/Hr; (vii) about 50-60 L/Hr; (viii) about 60-70 L/Hr; (ix) about 70-80 L/Hr; (x) about 80-90 L/Hr; (xi) about 90-100 L/Hr; (xii) about 100-150 L/Hr; (xiii) about 150-200 L/Hr; (xiv) about 200-250 L/Hr; (xv) about 250-300 L/Hr; (xvi) about 300-350 L/Hr; (xvii) about 350-400 L/Hr; (xviii) about 400-450 L/Hr; (xix) about 450-500 L/Hr; and (xx) about >500 L/Hr.

According to an embodiment Q1<Q2 or Q1>Q2.

The control system may be arranged and adapted to vary the gas flow, cone gas flow, auxiliary gas flow, makeup gas flow, reference gas flow or modifier gas flow as a function of time during the first period of time and/or the control system may be arranged and adapted to vary the gas flow, cone gas flow, auxiliary gas flow, makeup gas flow, reference gas flow or modifier gas flow as a function of time during the second period of time.

The control system may be arranged and adapted to operate the atmospheric pressure ionisation ion source at the one or more first settings for the first period of time upon detecting one or more background substances (e.g. solvents) eluting from the gas chromatography separation device and/or upon detecting one or more changes in an operating condition or operating efficiency of the ion source.

According to another aspect there is provided a method of mass spectrometry comprising:

operating an atmospheric pressure ionisation source at one or more first settings for a first period of time whilst one or more solvents elute from a gas chromatography separation device during a solvent front; and then operating the atmospheric pressure ionisation source at one or more second different settings for a second subsequent period of time whilst one or more analytes elute from the gas chromatography separation device.

According to an embodiment the mass spectrometer may further comprise:

(a) an ion source comprising an Atmospheric Pressure Photo Ionisation ("APPI") ion source, an Atmospheric Pressure Chemical Ionisation ("APCI") ion source, an Atmospheric Pressure Ionisation ("API") ion source, a Nickel-63 radioactive ion source, an Atmospheric Pressure Matrix Assisted Laser Desorption Ionisation ion source, an Atmospheric Sampling Glow Discharge Ionisation ("ASGDI") ion source, a Glow Discharge ("GD") ion source or an Impactor ion source; and/or (b) one or more continuous or pulsed ion sources; and/or (c) one or more ion guides; and/or (d) one or more ion mobility separation devices and/or one or more Field Asymmetric Ion Mobility Spectrometer devices; and/or (e) one or more ion traps or one or more ion trapping regions; and/or (f) one or more collision, fragmentation or reaction cells selected from the group consisting of: (i) a Collisional Induced Dissociation ("CID") fragmentation device; (ii) a Surface Induced Dissociation ("SID") fragmentation device; (iii) an Electron Transfer Dissociation ("ETD") fragmentation device; (iv) an Electron Capture Dissociation ("ECD") fragmentation device; (v) an Electron Collision or Impact Dissociation fragmentation device; (vi) a Photo Induced Dissociation ("PID") fragmentation device; (vii) a Laser Induced Dissociation fragmentation device; (viii) an infrared radiation induced dissociation device; (ix) an ultraviolet radiation induced dissociation device; (x) a nozzle-skimmer interface fragmentation device; (xi) an in-source fragmentation device; (xii) an in-source Collision Induced Dissociation fragmentation device; (xiii) a thermal or temperature source fragmentation device; (xiv) an electric field induced fragmentation device; (xv) a magnetic field induced fragmentation device; (xvi) an enzyme digestion or enzyme degradation fragmentation device; (xvii) an ion-ion reaction fragmentation device; (xviii) an ion-molecule reaction fragmentation device; (xix) an ion-atom reaction fragmentation device; (xx) an ion-metastable ion reaction fragmentation device; (xxi) an ion-metastable molecule reaction fragmentation device; (xxii) an ion-metastable atom reaction fragmentation device; (xxiii) an ion-ion reaction device for reacting ions to form adduct or product ions; (xxiv) an ion-molecule reaction device for reacting ions to form adduct or product ions; (xxv) an ion-atom reaction device for reacting ions to form adduct or product ions; (xxvi) an ion-metastable ion reaction device for reacting ions to form adduct or product ions; (xxvii) an ion-metastable molecule reaction device for reacting ions to form adduct or product ions; (xxviii) an ion-metastable atom reaction device for reacting ions to form adduct or product ions; and (xxix) an Electron Ionisation Dissociation ("EID") fragmentation device; and/or (g) a mass analyser selected from the group consisting of: (i) a quadrupole mass analyser; (ii) a 2D or linear quadrupole mass analyser; (iii) a Paul or 3D quadrupole mass analyser; (iv) a Penning trap mass analyser; (v) an ion trap mass analyser; (vi) a magnetic sector mass analyser; (vii) Ion Cyclotron Resonance ("ICR") mass analyser; (viii) a Fourier Transform Ion Cyclotron Resonance ("FTICR") mass analyser; (ix) an electrostatic mass analyser arranged to generate an electrostatic field having a quadro-logarithmic potential distribution; (x) a Fourier Transform electrostatic mass analyser; (xi) a Fourier Transform mass analyser; (xii) a Time of Flight mass analyser; (xiii) an orthogonal acceleration Time of Flight mass analyser; and (xiv) a linear acceleration Time of Flight mass analyser; and/or (h) one or more energy analysers or electrostatic energy analysers; and/or (i) one or more ion detectors; and/or (j) one or more mass filters selected from the group consisting of: (i) a quadrupole mass filter; (ii) a 2D or linear quadrupole ion trap; (iii) a Paul or 3D quadrupole ion trap; (iv) a Penning ion trap; (v) an ion trap; (vi) a magnetic sector mass filter; (vii) a Time of Flight mass filter; and (viii) a Wien filter; and/or (k) a device or ion gate for pulsing ions; and/or (l) a device for converting a substantially continuous ion beam into a pulsed ion beam.

The mass spectrometer may further comprise either:

(i) a C-trap and a mass analyser comprising an outer barrel-like electrode and a coaxial inner spindle-like electrode that form an electrostatic field with a quadro-logarithmic potential distribution, wherein in a first mode of operation ions are transmitted to the C-trap and are then injected into the mass analyser and wherein in a second mode of operation ions are transmitted to the C-trap and then to a collision cell or Electron Transfer Dissociation device wherein at least some ions are fragmented into fragment ions, and wherein the fragment ions are then transmitted to the C-trap before being injected into the mass analyser; and/or (ii) a stacked ring ion guide comprising a plurality of electrodes each having an aperture through which ions are transmitted in use and wherein the spacing of the electrodes increases along the length of the ion path, and wherein the apertures in the electrodes in an upstream section of the ion guide have a first diameter and wherein the apertures in the electrodes in a downstream section of the ion guide have a second diameter which is smaller than the first diameter, and wherein opposite phases of an AC or RF voltage are applied, in use, to successive electrodes.

According to an embodiment the mass spectrometer may further comprise a device arranged and adapted to supply an AC or RF voltage to the electrodes. The AC or RF voltage may have an amplitude selected from the group consisting of: (i) <50 V peak to peak; (ii) 50-100 V peak to peak; (iii) 100-150 V peak to peak; (iv) 150-200 V peak to peak; (v) 200-250 V peak to peak; (vi) 250-300 V peak to peak; (vii) 300-350 V peak to peak; (viii) 350-400 V peak to peak; (ix) 400-450 V peak to peak; (x) 450-500 V peak to peak; and (xi) >500 V peak to peak.

The AC or RF voltage may have a frequency selected from the group consisting of: (i) <100 kHz; (ii) 100-200 kHz; (iii) 200-300 kHz; (iv) 300-400 kHz; (v) 400-500 kHz; (vi) 0.5-1.0 MHz; (vii) 1.0-1.5 MHz; (viii) 1.5-2.0 MHz; (ix) 2.0-2.5 MHz; (x) 2.5-3.0 MHz; (xi) 3.0-3.5 MHz; (xii) 3.5-4.0 MHz; (xiii) 4.0-4.5 MHz; (xiv) 4.5-5.0 MHz; (xv) 5.0-5.5 MHz; (xvi) 5.5-6.0 MHz; (xvii) 6.0-6.5 MHz; (xviii) 6.5-7.0 MHz; (xix) 7.0-7.5 MHz; (xx) 7.5-8.0 MHz; (xxi) 8.0-8.5 MHz; (xxii) 8.5-9.0 MHz; (xxiii) 9.0-9.5 MHz; (xxiv) 9.5-10.0 MHz; and (xxv) >10.0 MHz.

The ion guide may be maintained at a pressure selected from the group consisting of: (i) <0.0001 mbar; (ii) 0.0001-0.001 mbar; (iii) 0.001-0.01 mbar; (iv) 0.01-0.1 mbar; (v) 0.1-1 mbar; (vi) 1-10 mbar; (vii) 10-100 mbar; (viii) 100-1000 mbar; and (ix) >1000 mbar.

According to another aspect there is provided a mass spectrometer comprising:

a gas chromatography separation device;

an atmospheric pressure ionisation ion source; and a control system arranged and adapted:

(i) to operate the atmospheric pressure ionisation ion source at one or more first settings for a first period of time whilst one or more background substances elute from the gas chromatography separation device; and then (ii) to operate the atmospheric pressure ionisation ion source at one or more second different settings for a second subsequent period of time whilst one or more analytes elute from the gas chromatography separation device.

According to another aspect there is provided a method of mass spectrometry comprising:

operating an atmospheric pressure ionisation source at one or more first settings for a first period of time whilst one or more background substances elute from a gas chromatography separation device; and then operating the atmospheric pressure ionisation source at one or more second different settings for a second subsequent period of time whilst one or more analytes elute from the gas chromatography separation device.

BRIEF DESCRIPTION OF THE DRAWINGS

Various embodiments will now be described together with other arrangements given for illustrative purposes only, by way of example only, and with reference to the accompanying drawings in which.

DETAILED DESCRIPTION

Various embodiments will now be described.

Figure 4:
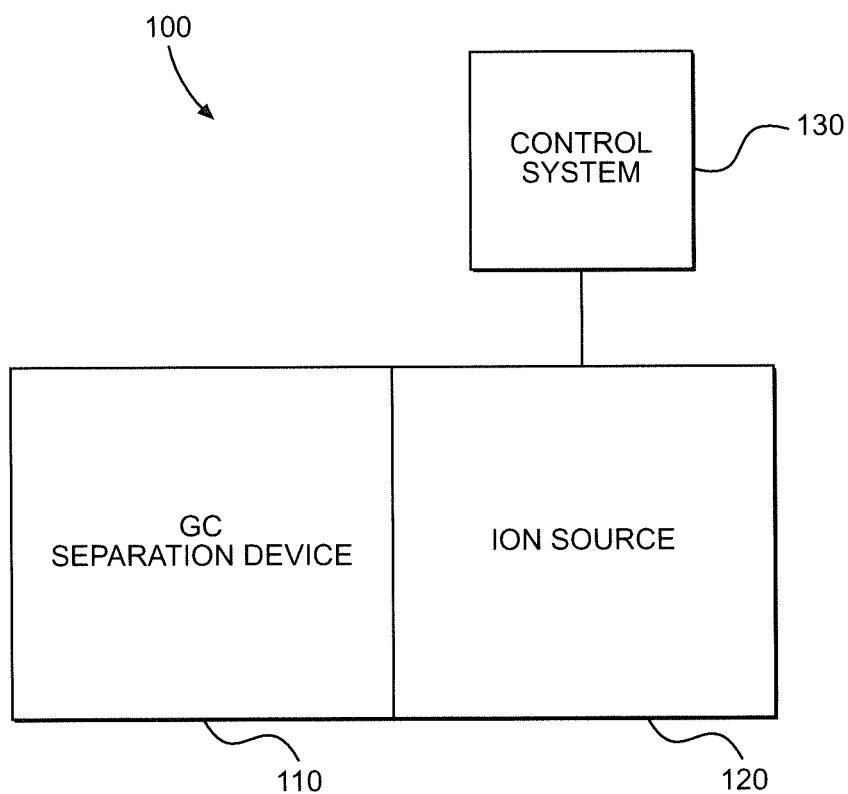
FIG. 4 shows an aspect of the present invention, a mass spectrometer comprising a gas chromatography separation device, an atmospheric pressure ionisation ion source, and a control system.

FIG. 4 shows a preferred embodiment of the present invention, a mass spectrometer 100 comprising:

a gas chromatography separation device 110;
an atmospheric pressure ionisation ion source 120; and
a control system 130 arranged and adapted:

(i) to operate said atmospheric pressure ionisation ion source 120 at one or more first settings for a first period of time whilst one or more solvents elute from said gas chromatography separation device 110 during a solvent front; and then (ii) to operate said atmospheric pressure ionisation ion source 120 at one or more second different settings for a second subsequent period of time whilst one or more analytes elute from said gas chromatography separation device 110.

During routine gas chromatography analysis, the elution of analytes from the gas chromatography column is preceded by the elution of vaporised solvent in which the analytes were contained and this effect is commonly referred to as a solvent front. The solvent front can disrupt the ion source ionisation conditions of the mass spectrometer and lead to significant differences in analyte response from one analysis to the next.

The embodiment results in improved reproducibility by the adjustment of various ion source conditions during the elution of the solvent.

The approach according to the embodiment is particularly advantageous in that the embodiment significantly improves the reproducibility of the detection of analytes of interest. This has various benefits including improved quantitative precision and more reliable analysis.

In particular, several methods have been developed in order to improve the reproducibility of the analysis. These methods involve altering one or more ion source conditions during the elution of a solvent front and then reverting to standard operational conditions for the remainder of the acquisition.

A number of methods are discussed below which have the effect of significantly improving reproducibility of subsequent analyses by reducing the variation in the corona pin regulation voltage after the elution of a solvent front. Other methods involve varying the gas flows within the ionisation volume in order to minimise the influence of the solvent front on subsequent analysis.

According to embodiments various aspects of the ion source conditions may be synchronised.

According to an embodiment the corona pin current may be regulated. A regulation value may be achieved by the application of a voltage to the corona pin. A typical operating current is around 2 µA and is typically achieved with the application of around 1600 V to the corona pin.

According to an embodiment the cone gas flow (e.g. nitrogen) introduced around the sampling orifice of the mass spectrometer may be controlled. This gas partially ballasts the pumping requirements of the orifice and thereby dictates the flow of sample gases from the source environment into the analyser section of the mass spectrometer.

According to an embodiment the auxiliary gas flow may be controlled. A gas (e.g. nitrogen) may be introduced into the ion source enclosure in order to maintain a steady flow of gas through the chamber so as to help purge sample gases and maintain a consistent environment.

According to various embodiment the corona pin may be set to regulate at 0 µA or substantially lowered during the solvent front elution.

According to other embodiments the corona pin may be set to an abnormally high current and/or the cone gas flow may be turned OFF or substantially lowered.

According to another embodiment the cone gas may be lowered to an intermediate value between the acquisition setting and zero.

According to an embodiment the cone gas may be lowered and/or the auxiliary gas flow may be increased.

According to another embodiment the corona pin and the cone gas flow may both be set to 0 µA and 0 L/Hr, or substantially lowered.

According to an embodiment the corona pin current may be raised and the cone gas flow may be turned OFF or substantially lowered.

According to another embodiment the corona pin and the cone gas flow may be set to 0 µA and 0 L/Hr, or substantially lowered and the auxiliary flow may be increased.

The above described embodiments have been shown to provide an advantage over conventional arrangements.

According to the embodiment normal operating conditions are preferably restored once the solvent front has passed and prior to the elution of analytes.

Various examples illustrating a number of different embodiments and the improvement in reproducibility will now be described.

Figure 5:
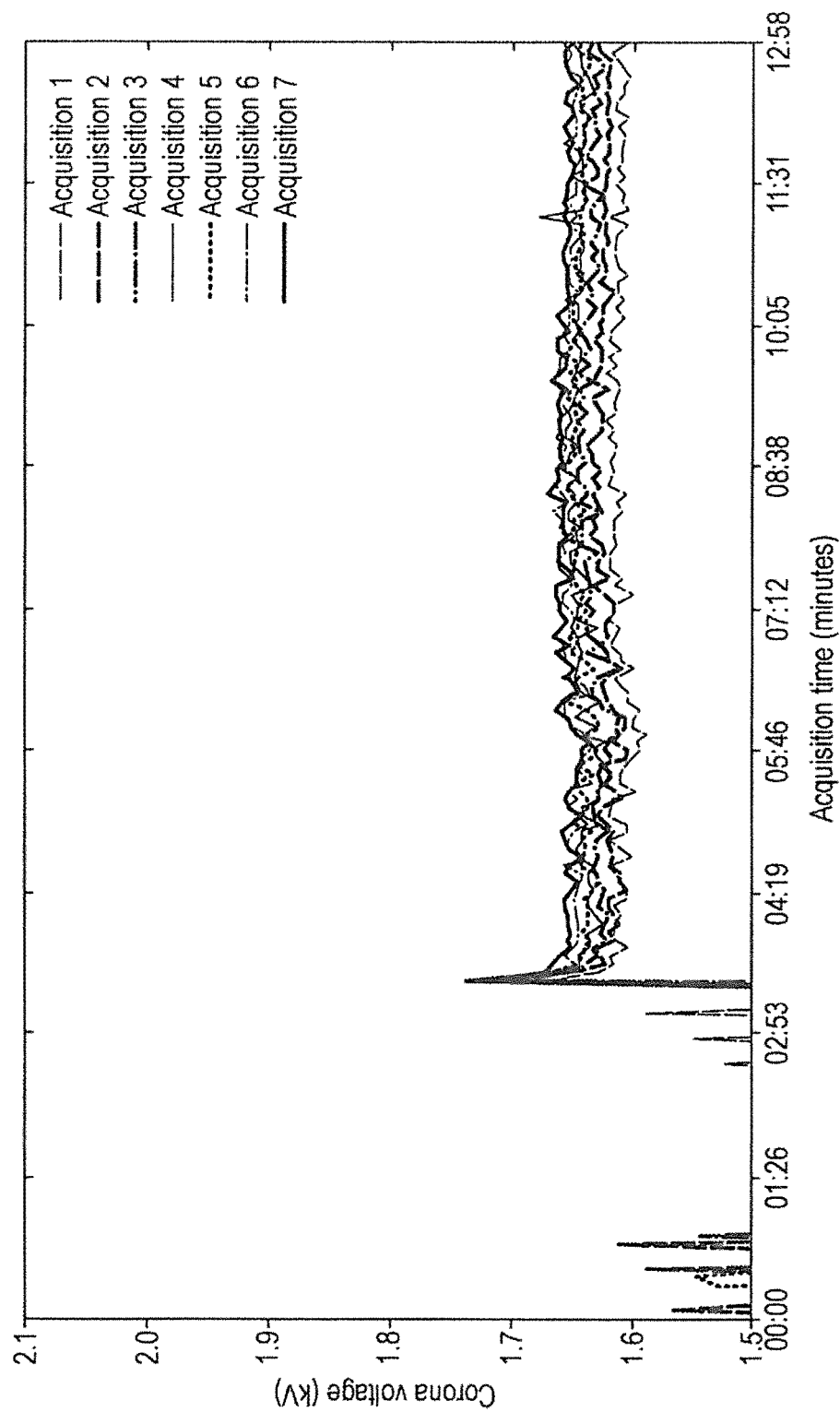
FIG. 5 illustrates an embodiment wherein the corona pin of an atmospheric pressure chemical ionisation ion source is set to regulate at 0 µA during a solvent front and wherein the voltage which is subsequently applied to the corona pin in order to regulate or maintain the corona current at 2.0 µA for analyte analysis is stablised.

FIG. 5 illustrates an embodiment wherein the analysis was repeated but wherein the corona current was set to 0.0 µA during the elution of the solvent front between an acquisition time of 0 minutes to 3.5 minutes. At 3.5 minutes acquisition time, the corona current was set to a conventional operating value of 2.0 µA.

Figure 1:
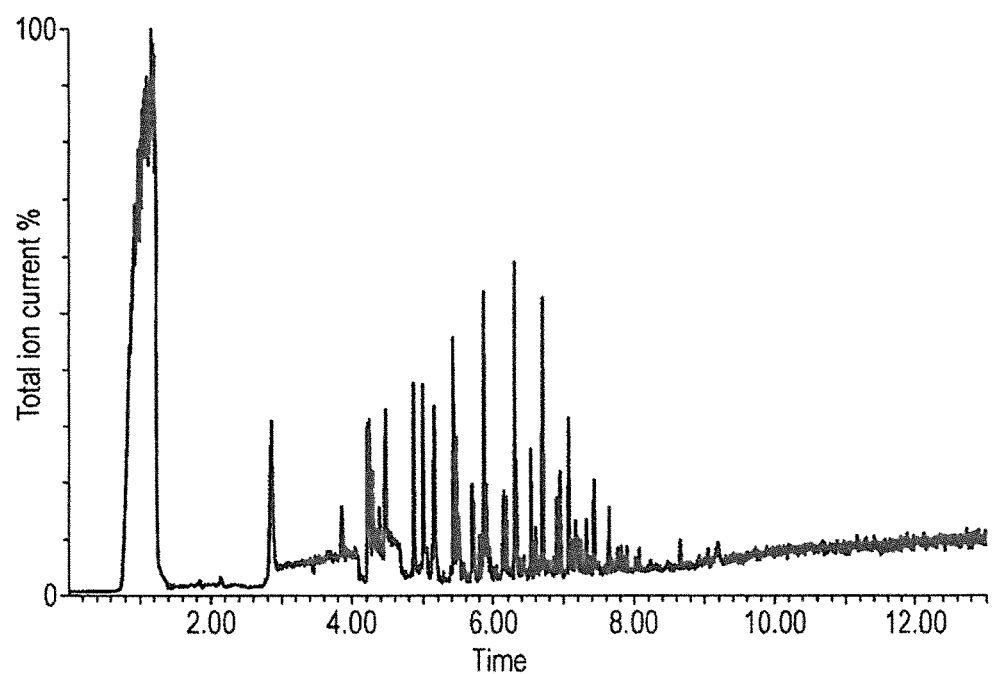
FIG. 1 shows the total ion current of a gas chromatograph-atmospheric pressure chemical ionisation MS acquisition showing a solvent front which causes a significant rise in the total ion current between 0.7 and 1.5 minutes from the start of the analysis.
Figure 2:
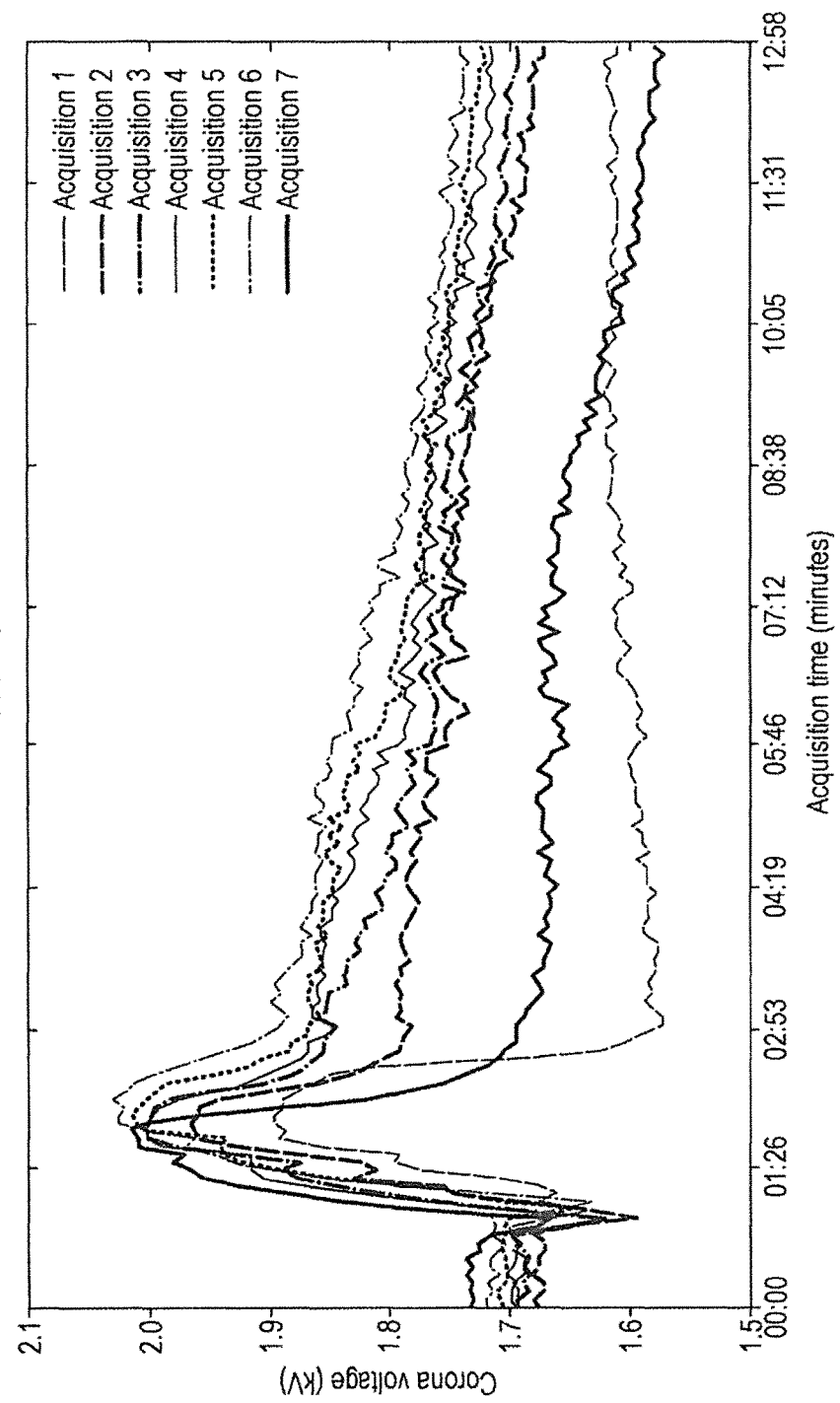
FIG. 2 shows the voltage applied to a corona pin of an atmospheric pressure chemical ionisation ion source during seven sequential acquisitions in order to regulate or maintain the corona current at 2.0 µA.
Figure 3:
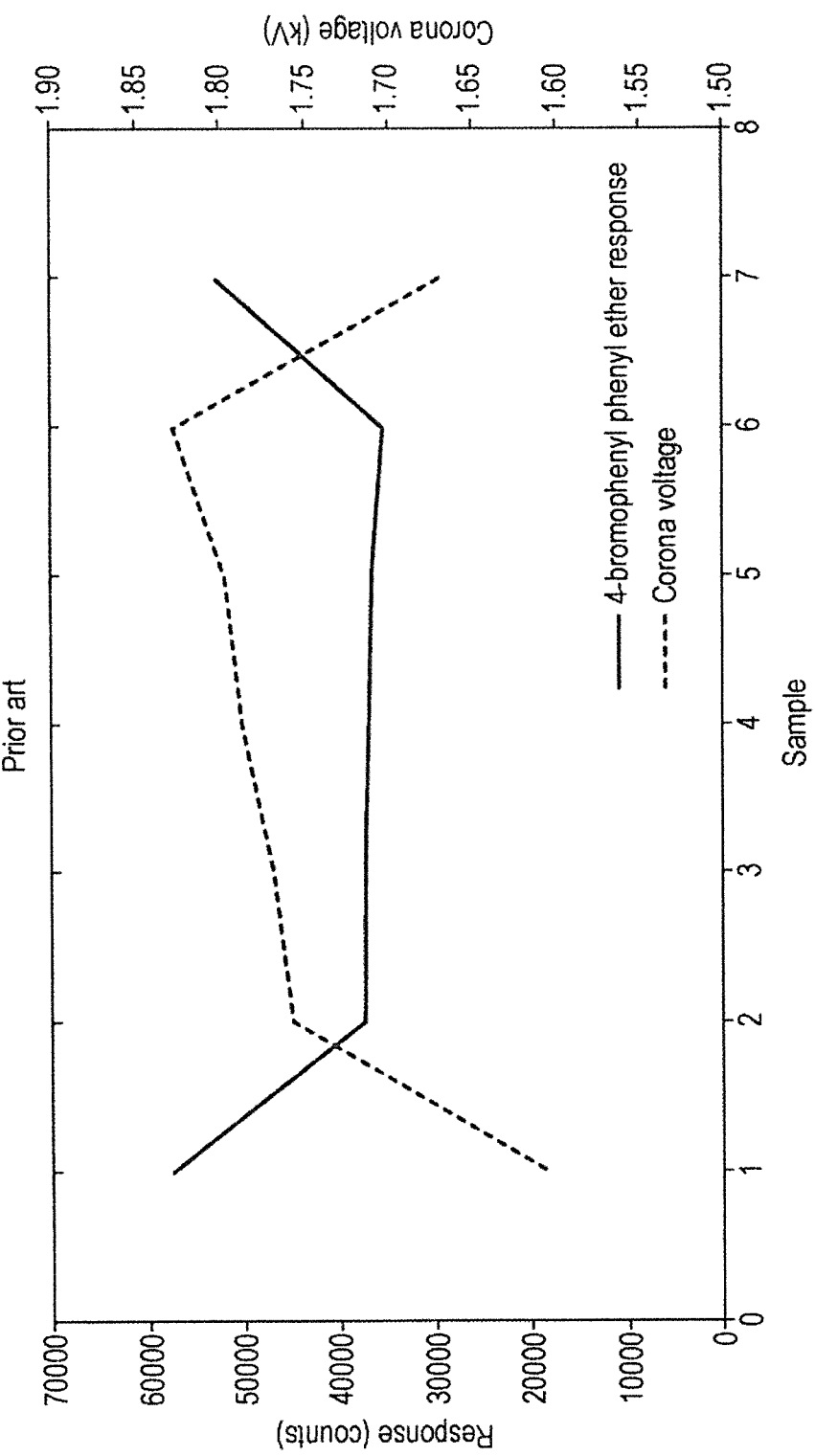
FIG. 3 shows the highly variable response of 4-bromophenyl phenyl ether according to a conventional arrangement.

It is apparent from FIG. 5 that the voltage required in order to regulate or maintain the corona current at 2.0 µA is now more reproducible from one acquisition to the next compared with the conventional approach as illustrated in FIG. 2.

The response of the analyte as shown FIG. 5 shows a marked improvement in reproducibility corresponding to the improvement in corona voltage reproducibility and stability.

The peak responses of a number of the analytes within the samples being analysed when the corona pin is left ON during the solvent front according to a conventional approach is shown in Table 1 below.

TABLE 1 peak responses for seven analyses with no solvent front modification

| Species | Peak Responses for Sample | | | | | | | RSD (%) |
|---|---|---|---|---|---|---|---|---|
| | 1 | 2 | 3 | 4 | 5 | 6 | 7 | |
| 2-Chlorophenol | 24423 | 15165 | 15053 | 14186 | 14026 | 13648 | 21554 | 25.49 |
| Dichlorobenzenes | 45227 | 31942 | 30657 | 29897 | 28277 | 29011 | 39736 | 19.14 |
| 1,2,4-trichlorobenzene | 45269 | 34272 | 33551 | 33104 | 31884 | 31912 | 41596 | 14.73 |
| 4-chloro-3-methyl phenol | 30658 | 21117 | 19392 | 18469 | 18149 | 17916 | 27307 | 23.22 |
| Fluorene | 75979 | 67873 | 67739 | 68294 | 67550 | 66718 | 78353 | 6.72 |
| 4-bromophenyl phenyl ether | 57425 | 37387 | 37263 | 36844 | 36544 | 35443 | 52702 | 21.67 |
| Hexachlorobenzene | 44527 | 35398 | 36544 | 35244 | 34990 | 33317 | 39557 | 10.25 |
| Phenanthrene | 95909 | 91380 | 87949 | 90729 | 91276 | 90984 | 101226 | 4.74 |
| Fluoroanthene | 101101 | 92023 | 93970 | 91613 | 90363 | 91889 | 99168 | 4.41 |
| Pyrene | 98567 | 87626 | 90447 | 83867 | 87478 | 85103 | 95081 | 5.98 |
| Chrysene | 88866 | 82180 | 87078 | 74271 | 75352 | 80653 | 81991 | 6.66 |
| Benzo(g,h,l)perylene | 52177 | 54557 | 54263 | 42603 | 45118 | 42739 | 44062 | 11.44 |
| | | | | | | | Average = | 12.87 |

In contrast, the peak responses when the corona pin is set to regulate at 0 µA during a solvent front according to an embodiment is shown in Table 2 below.

The data shown in Table 2 demonstrates a significant improvement in the relative standard deviation ("RSD") according to the embodiment as a result of controlling the corona pin in a manner according to the embodiment.

The benefit of controlling the corona pin in this fashion is more apparent for the analytes which elute closest to the solvent front. The analytes listed in Tables 1 and 2 are given in elution order with 2-Chlorophenol being the first eluting analyte and Benzo(g,h,i)perylene being the last.

conditions were made during the solvent front (100 injections). Test 2 was performed wherein the corona current was set to 20.0 µA during the solvent front (57 injections). Finally, test 3 was performed wherein the corona current was set to 20.0 µA and wherein the cone gas flow rate was reduced to 0 L/Hr during the solvent front (83 injections).

Figure 7:
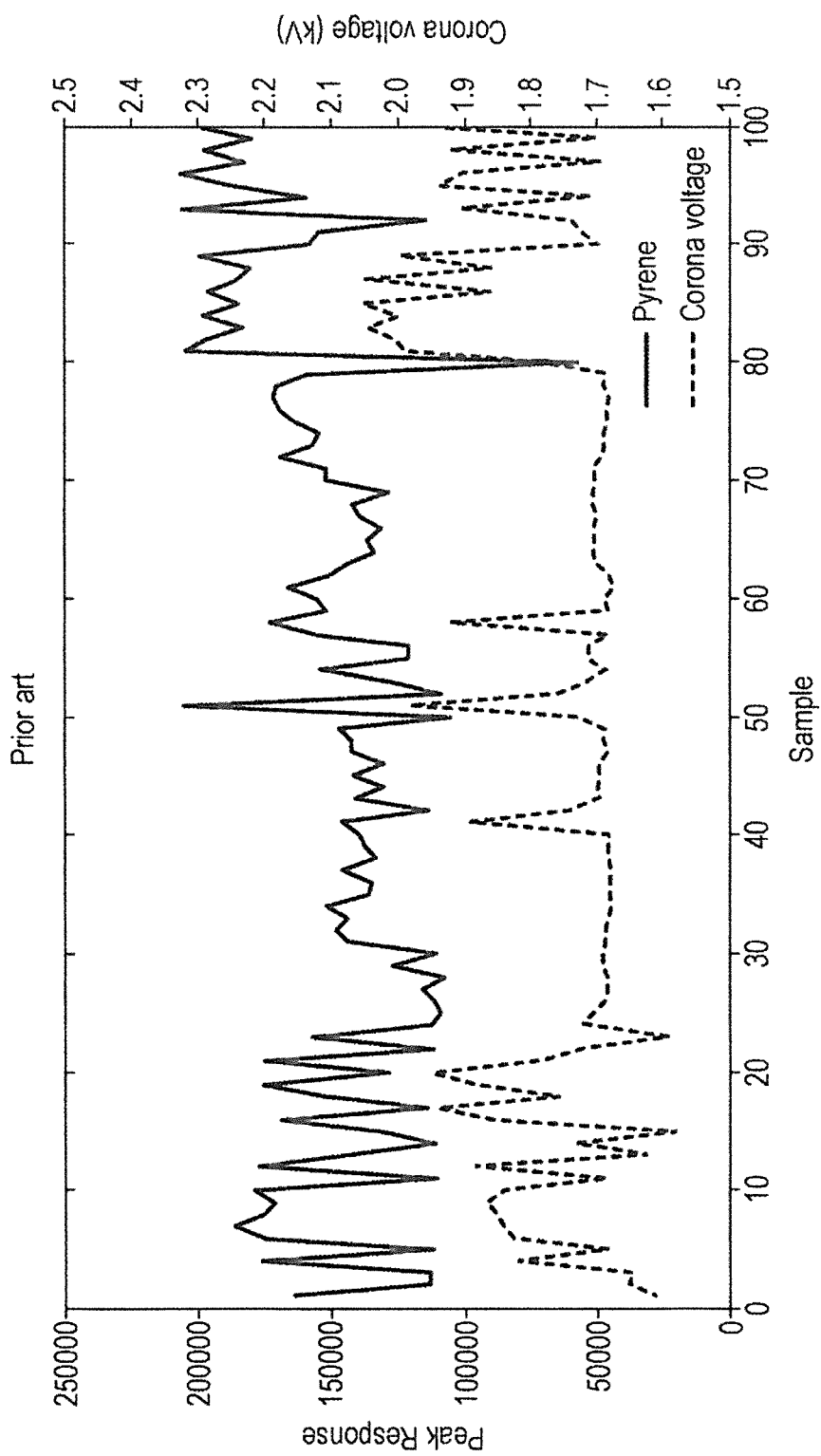
FIG. 7 shows the highly variable response of pyrene with no modification made during a solvent front in accordance with a conventional approach.
Figure 8:
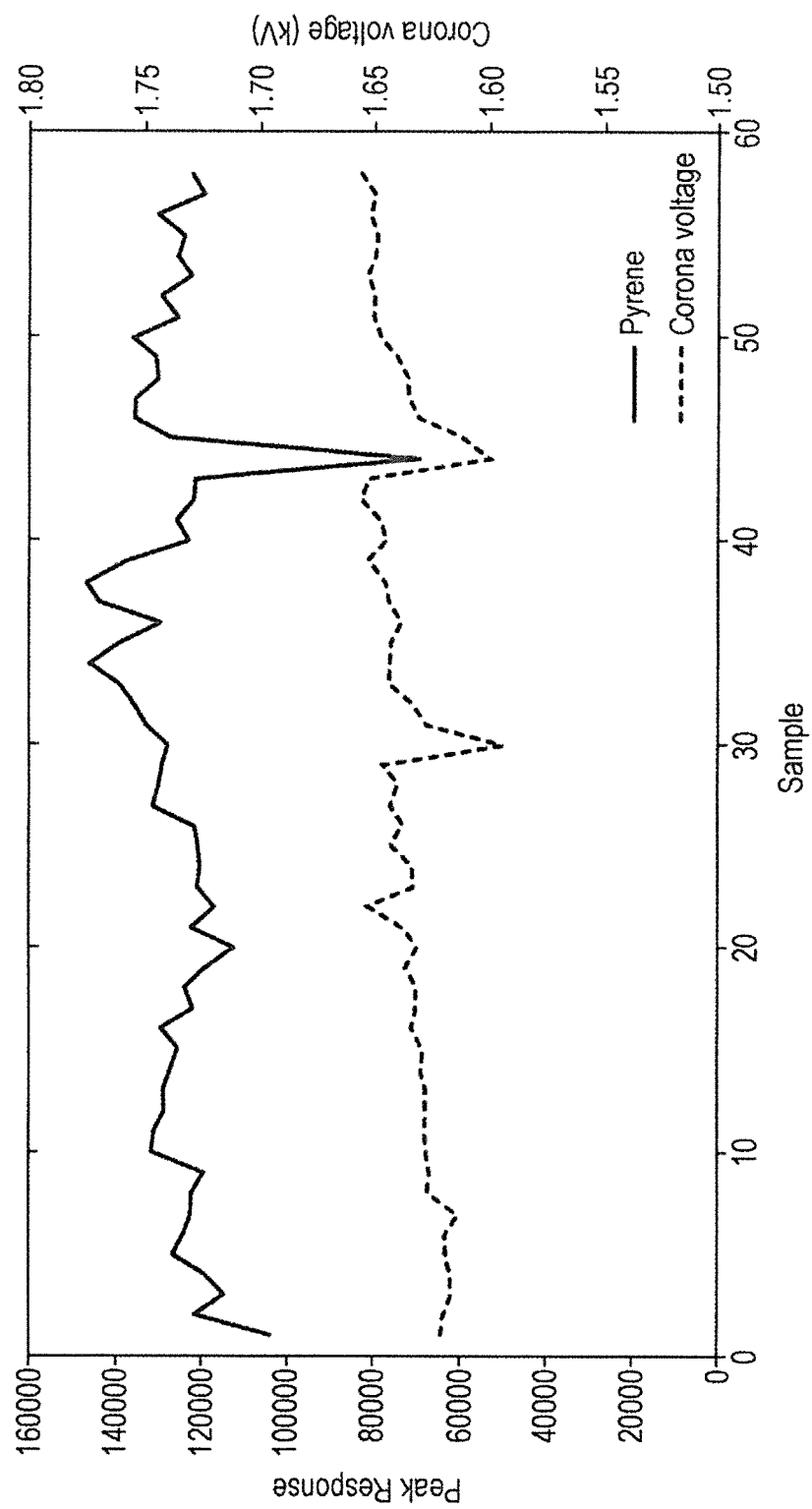
FIG. 8 shows the improved response of pyrene according to an embodiment wherein the corona current was raised to 20 µA during a solvent front.
Figure 9:
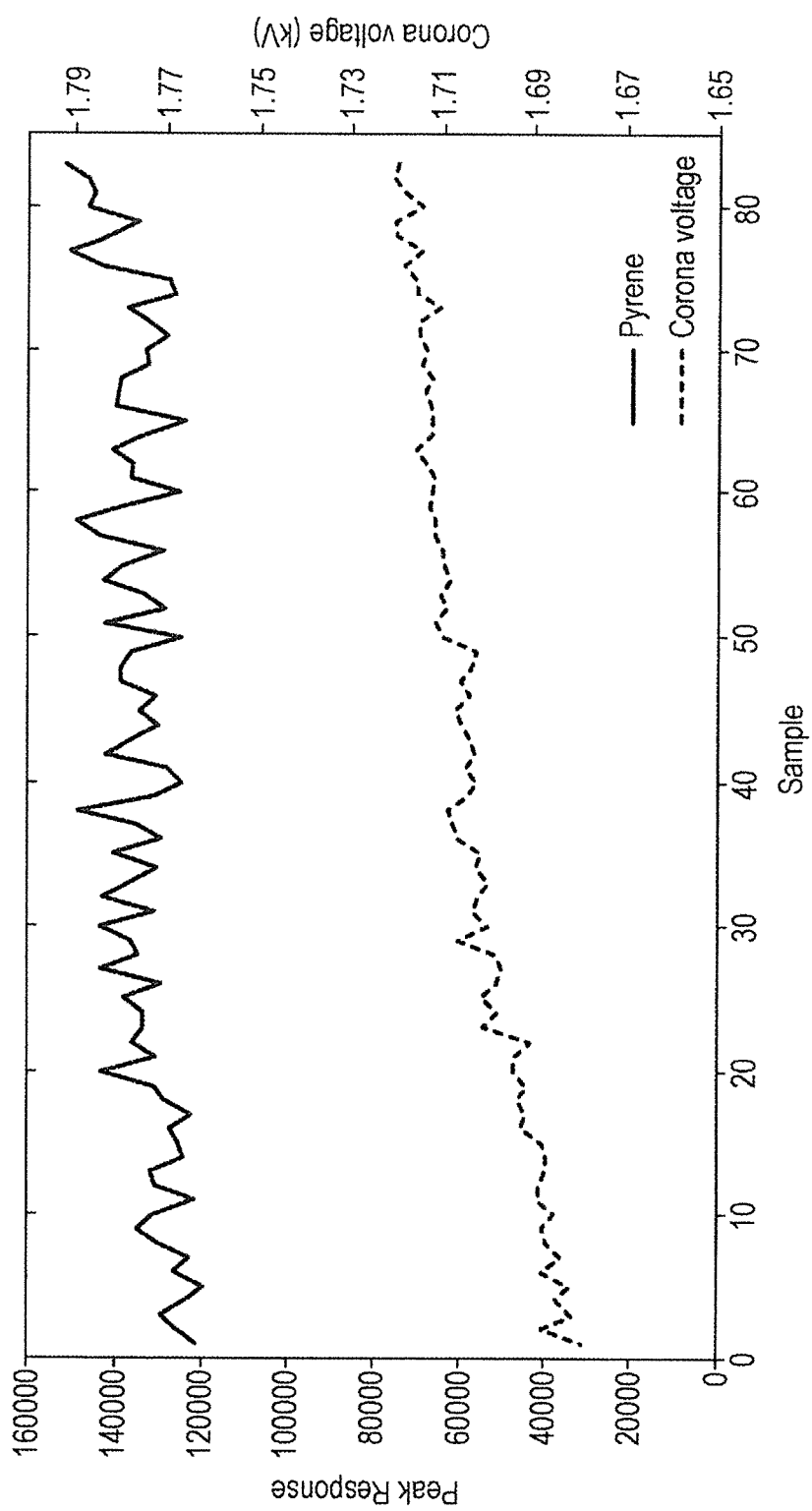
FIG. 9 shows the improved response of pyrene according to an embodiment wherein the corona current was raised to 20 µA and wherein the cone gas flow was dropped to 0 L/Hr during a solvent front.

The response for one of the major analytes (pyrene) within the samples analysed under the three test conditions detailed above together with the applied corona voltage are shown in FIGS. 7, 8, 9.

FIG. 7 shows the response of pyrene with no modification during a solvent front i.e. according to a conventional approach.

FIG. 8 shows the improved response of pyrene wherein the corona current was raised to 20 µA during a solvent front in accordance with an embodiment.

TABLE 2 peak responses for seven analyses with corona pin at 0 µA during solvent front

| Species | Peak Responses for Sample | | | | | | | RSD (%) |
|---|---|---|---|---|---|---|---|---|
| | 1 | 2 | 3 | 4 | 5 | 6 | 7 | |
| 2-Chlorophenol | 22715 | 23112 | 22954 | 22002 | 21504 | 20015 | 19391 | 6.76 |
| Dichlorobenzenes | 41087 | 42663 | 42356 | 41670 | 39969 | 39040 | 38555 | 3.95 |
| 1,2,4-trichlorobenzene | 41599 | 43439 | 43082 | 42546 | 41535 | 39861 | 40391 | 3.20 |
| 4-chloro-3-methyl phenol | 29142 | 30931 | 31763 | 29449 | 28802 | 26621 | 25936 | 7.28 |
| Fluorene | 76178 | 75455 | 74712 | 75682 | 75533 | 73536 | 73919 | 1.30 |
| 4-bromophenyl phenyl ether | 50146 | 49405 | 49058 | 48092 | 47827 | 47184 | 46390 | 2.72 |
| Hexachlorobenzene | 41725 | 43297 | 42216 | 41478 | 41850 | 39252 | 38994 | 3.81 |
| Phenanthrene | 98100 | 97895 | 97564 | 96419 | 97315 | 94057 | 94257 | 1.76 |
| Fluoroanthene | 105317 | 101552 | 102263 | 99436 | 97236 | 96751 | 97386 | 3.19 |
| Pyrene | 99641 | 100344 | 99115 | 100219 | 95016 | 90126 | 95326 | 3.92 |
| Chrysene | 94717 | 93617 | 94701 | 89219 | 92111 | 84565 | 83357 | 5.26 |
| Benzo(g,h,l)perylene | 51170 | 57451 | 60291 | 51273 | 59127 | 47147 | 53277 | 8.91 |
| | | | | | | | Average = | 4.34 |

Figure 6:
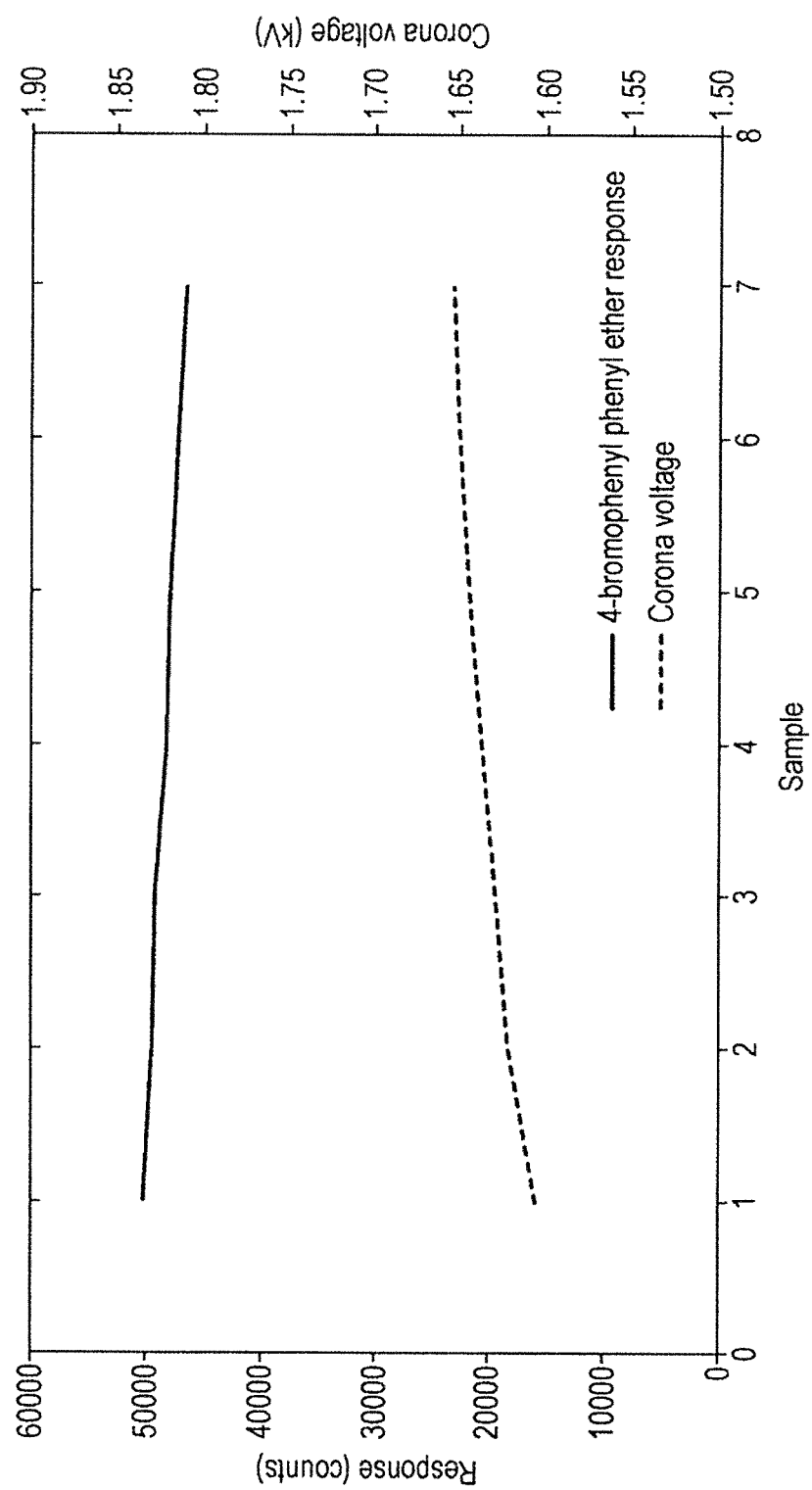
FIG. 6 shows the significantly improved response of 4-bromophenyl phenyl ether according to a embodiment wherein the corona current is set at 0 µA during an initial solvent front.

FIG. 6 shows the significantly improved response of 4-bromophenyl phenyl ether according to a embodiment wherein the corona current is set at 0 µA during an initial solvent front.

A more comprehensive experiment studying the effect of varying source conditions during a solvent front was conducted using three sets of test conditions as follows. Test 1 was performed wherein no modification to the ion source FIG. 9 shows the improved response of pyrene wherein the corona current was raised to 20 µA and wherein the cone gas flow was reduced to 0 L/Hr during a solvent front.

It is apparent from FIG. 8 that setting the corona current to a high value (e.g. 20 µA) according to an embodiment during a solvent front subsequently helped stabilise the corona after the solvent front had passed with a resultant improvement in reproducibility.

It is also apparent from FIG. 9 that setting the cone gas flow to 0 L/Hr whilst also raising the corona current to 20 μA during the passing of a solvent front provided a further improvement in stability.

Removing the cone gas flow has the effect of increasing the flow of gases from within the source enclosure through the sampling orifice of the mass spectrometer and therefore helps purge the source region of the vaporised solvent from the gas chromatography column.

A comparison of the peak responses and relative standard deviations of the peak responses and corona voltages under the three test conditions is given in Table 3 below.

TABLE 3

Comparison of the peak responses and stability under the three test conditions

| Species | Average Peak Response | | | Relative Standard Deviation (%) | | | RSD of Corona Voltage (%) | | |
|---|---|---|---|---|---|---|---|---|---|
| | 1 | 2 | 3 | 1 | 2 | 3 | 1 | 2 | 3 |
| 4-chloro-3-methylphenol | 18525 | 24030 | 22925 | 22.0 | 10.2 | 7.6 | 6.34 | 0.80 | 0.68 |
| Fluorene | 71022 | 80487 | 78809 | 21.9 | 10.0 | 4.4 | 6.18 | 0.85 | 0.70 |
| Hexachlorobenzene | 4914 | 4966 | 4933 | 18.0 | 7.9 | 6.6 | 6.12 | 0.86 | 0.66 |
| Phenanthrene | 39453 | 39498 | 41275 | 22.0 | 9.6 | 4.1 | 6.13 | 0.82 | 0.64 |
| Fluoroanthene | 147545 | 125597 | 139075 | 19.6 | 8.6 | 5.5 | 6.39 | 0.83 | 0.65 |
| Pyrene | 150455 | 125900 | 134085 | 19.4 | 8.7 | 5.6 | 6.43 | 0.83 | 0.64 |
| Chrysene | 162128 | 144829 | 164820 | 21.1 | 10.7 | 6.0 | 6.67 | 0.82 | 0.68 |
| Indeno(1,2,3-cd)pyrene | 13889 | 11229 | 12448 | 15.8 | 13.9 | 12.1 | 6.62 | 0.88 | 0.67 |
| Benzo(g,h,l)pyrene | 14164 | 11006 | 12352 | 16.0 | 13.2 | 11.6 | 6.58 | 0.94 | 0.68 |

An experiment was conducted in order to study the effect of varying the auxiliary gas flow in conjunction with the cone gas flow. When the cone gas flow was reduced there is an increase in the flow of gasses from the source enclosure through the sampling orifice and into the mass spectrometer. If there is insufficient gas being introduced into the source enclosure when the cone gas flow is reduced then it is possible to draw in gases from the exhaust port of the enclosure which potentially can lead to contamination.

In order to prevent this from occurring, during this experiment the auxiliary gas flow was increased at the same time as the cone gas flow was reduced.

Two ion source conditions were tested in this experiment. Test 1 was performed wherein the corona current was set to 0.0 μA during the solvent front (40 injections). Test 2 was performed wherein the corona current was set to 0.0 μA and wherein the cone gas flow was set to 50 L/Hr and at the same time the auxiliary gas flow was set to 400 L/Hr during the passing of the solvent front (40 injections).

Figure 10:
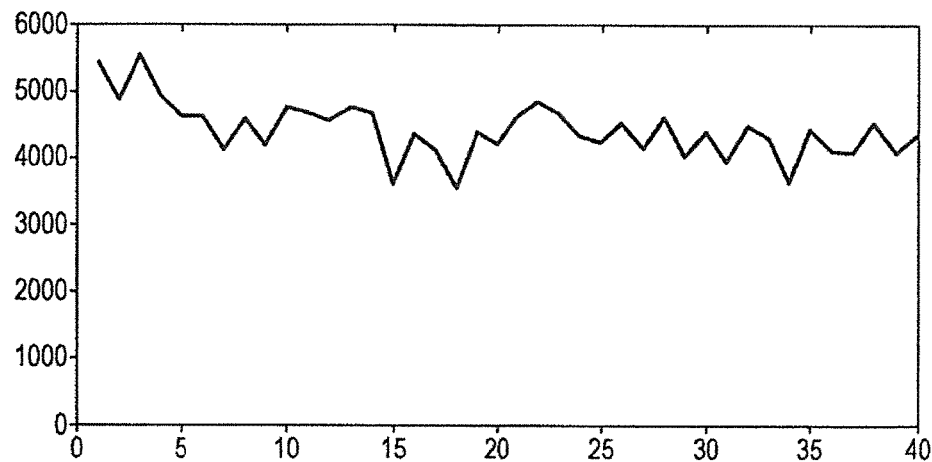
FIG. 10 shows the improved response of 2,3,7,8 ($^{13}C_{12}$) TCDD according to an embodiment wherein the corona current was set to regulate at 0 µA during a solvent front.
Figure 11:
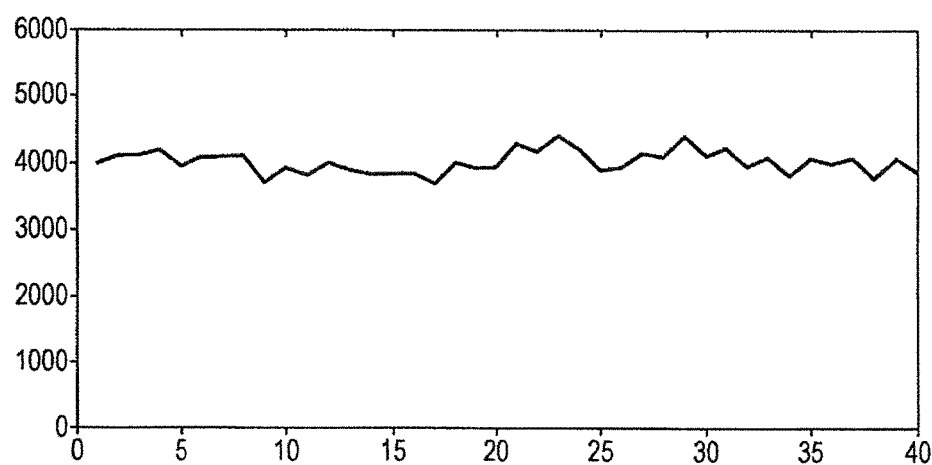
FIG. 11 shows the improved response of 2,3,7,8 ($^{13}C_{12}$) TCDD according to an embodiment wherein the corona current was set to regulate at 0 µA, the cone gas flow rate was set at 50 L/Hr and wherein an auxiliary gas flow rate was set at 400 L/Hr during a solvent front.

The peak responses for one of the principal analytes 2,3,7,8 ($^{13}C_{12}$) TCDD under these two sets of conditions are shown in FIGS. 10 and 11. FIG. 10 shows the response of 2,3,7,8 ($^{13}C_{12}$) TCDD with corona current at 0 μA during solvent front (Test 1). FIG. 11 shows the response of 2,3,7,8 ($^{13}C_{12}$) TCDD with corona current at 0 μA, cone gas at 50 L·Hr$^{-1}$ and auxiliary gas 400 L·Hr$^{-1}$ during solvent front (Test 2). A comparison of the responses and relative standard deviations for all analytes within the samples is given in Table 4 below.

It is apparent that there is a significant improvement in reproducibility as a result of varying the cone and auxiliary gas flows in conjunction with the setting of the corona current to 0 μA during the passing of a solvent front.

TABLE 4

Comparison of responses and reproducibility for Tests 1 and 2

| | Peak Response | | RSD (%) | |
|---|---|---|---|---|
| Species | 1 | 2 | 1 | 2 |
| 2,3,7,8 Tetrachlorodibenzo-p-dioxin | 427 | 273 | 10.5 | 4.8 |
| 1,2,3,4 Tetrachlorodibenzo-p-dioxin C13 | 5128 | 3632 | 9.0 | 4.4 |
| 2,3,7,8 Tetrachlorodibenzo-p-dioxin C13 | 4157 | 2681 | 8.7 | 4.5 |
| 2,3,7,8 Tetrachlorodibenzo-p-dioxin 4Cl37 | 814 | 532 | 9.1 | 3.7 |

TABLE 4-continued

Comparison of responses and reproducibility for Tests 1 and 2

| | Peak Response | | RSD (%) | |
|---|---|---|---|---|
| Species | 1 | 2 | 1 | 2 |
| 2,3,7,8 Tetrachlorodibenzofuran | 421 | 377 | 10.2 | 5.6 |
| 2,3,7,8 Tetrachlorodibenzofuran C13 | 4430 | 4011 | 9.5 | 4.3 |
| 1,2,3,7,8 Pentachlorodibenzo-p-dioxin | 2027 | 1411 | 9.4 | 4.6 |
| 1,2,3,7,8 Pentachlorodibenzo-p-dioxin C13 | 3931 | 2757 | 9.7 | 3.9 |
| 1,2,3,7,8 Pentachlorodibenzofuran | 2169 | 1721 | 9.5 | 5.3 |
| 2,3,4,7,8 Pentachlorodibenzofuran | 2233 | 1712 | 9.2 | 4.5 |
| 1,2,3,7,8 Pentachlorodibenzofuran C13 | 4541 | 3709 | 8.5 | 4.5 |
| 2,3,4,7,8 Pentachlorodibenzofuran C13 | 4477 | 3522 | 9.1 | 4.7 |
| 1,2,3,4,7,8 Hexachlorodibenzo-p-dioxin | 1714 | 1314 | 11.1 | 5.5 |
| 1,2,3,6,7,8 Hexachlorodibenzo-p-dioxin | 1787 | 1350 | 9.6 | 6.6 |
| 1,2,3,7,8,9 Hexachlorodibenzo-p-dioxin | 1495 | 1111 | 9.2 | 6.3 |
| 1,2,3,4,7,8 Hexachlorodibenzo-p-dioxin C13 | 3296 | 2525 | 9.6 | 6.6 |
| 1,2,3,6,7,8 Hexachlorodibenzo-p-dioxin C13 | 3735 | 2801 | 10.1 | 7.3 |
| 1,2,3,7,8,9 Hexachlorodibenzo-p-dioxin C13 | 2840 | 2197 | 9.5 | 6.3 |
| 1,2,3,6,7,8 Hexachlorodibenzofuran | 1739 | 1366 | 10.2 | 5.2 |
| 2,3,4,6,7,8 Hexachlorodibenzofuran | 1950 | 1537 | 9.1 | 5.9 |
| 1,2,3,4,7,8 Hexachlorodibenzofuran | 1916 | 1500 | 9.2 | 5.3 |
| 1,2,3,7,8,9 Hexachlorodibenzofuran | 1696 | 1236 | 9.3 | 5.4 |
| 1,2,3,6,7,8 Hexachlorodibenzofuran C13 | 3553 | 2821 | 9.8 | 5.2 |
| 2,3,4,6,7,8 Hexachlorodibenzofuran C13 | 3996 | 3240 | 9.9 | 5.9 |
| 1,2,3,4,7,8 Hexachlorodibenzofuran C13 | 3716 | 2940 | 9.6 | 5.1 |
| 1,2,3,7,8,9 Hexachlorodibenzofuran C13 | 3704 | 2738 | 9.2 | 5.5 |
| 1,2,3,4,6,7,8 Heptachlorodibenzo-p-dioxin | 1377 | 1140 | 10.3 | 6.1 |
| 1,2,3,4,6,7,8 Heptachlorodibenzo-p-dioxin C13 | 2667 | 2235 | 10.0 | 6.0 |
| 1,2,3,4,6,7,8 Heptachlorodibenzofuran | 1602 | 1286 | 10.2 | 5.6 |
| 1,2,3,4,7,8,9 Heptachlorodibenzofuran | 1365 | 1087 | 9.9 | 5.8 |
| 1,2,3,4,6,7,8 Heptachlorodibenzofuran C13 | 3202 | 2612 | 9.9 | 5.5 |
| 1,2,3,4,7,8,9 Heptachlorodibenzofuran C13 | 2711 | 2190 | 10.2 | 5.5 |
| Octachlorodibenzo-p-dioxin | 2365 | 2066 | 11.5 | 6.0 |
| Octachlorodibenzo-p-dioxin C13 | 4645 | 4243 | 11.6 | 5.7 |
| Octachlorodibenzofuran | 2372 | 2031 | 11.5 | 6.1 |
| Average RSD: | | | 9.8 | 5.4 |

Although the various embodiments described above focus upon increasing the corona current during a solvent front, other embodiments are also contemplated wherein other parameters may be varied. In particular, embodiments are contemplated wherein the corona voltage, corona polarity, ion source temperature, ion source voltage offset, cone voltage offset, makeup gas flow, a reference gas flow or a modifier gas flow may be varied during the passing of a solvent front and wherein the parameters are then reset to normal operating conditions when analysing analytes which subsequently elute from the gas chromatograph.

Embodiments are also contemplated wherein the one or more changes in the ion source conditions may be arranged to vary continuously or in a stepped manner during the elution of a solvent front. For example, according to an embodiment the one or more changes in the ion source conditions may be arranged to follow a pre-defined ramp or program.

The changes in ion source conditions may be triggered automatically in response to the detection of the solvent front through other means such as changes in corona efficiency or pressure changes.

Although the present invention has been described with reference to embodiments, it will be understood by those skilled in the art that various changes in form and detail may be made without departing from the scope of the invention as set forth in the accompanying claims.

The invention claimed is:

1. A mass spectrometer comprising:
a gas chromatography separation device;
an atmospheric pressure ionisation ion source; and
a control system arranged and adapted:
(i) to operate said atmospheric pressure ionisation ion source at one or more first settings for a first period of time whilst one or more solvents elute from said gas chromatography separation device during a solvent front free of analytes which is prior to the elution of one or more analytes from said gas chromatography separation device; and then
(ii) to operate said atmospheric pressure ionisation ion source at one or more second different settings for a second subsequent period of time whilst said one or more analytes elute from said gas chromatography separation device.

2. A mass spectrometer as claimed in claim 1, wherein said gas chromatography separation device comprises a gas chromatography column.

3. A mass spectrometer as claimed in claim 1, wherein said atmospheric pressure ionisation ion source comprises an Atmospheric Pressure Chemical Ionisation ("APCI") ionisation source.

4. A mass spectrometer as claimed in claim 3, wherein said Atmospheric Pressure Chemical Ionisation ("APCI") ionisation source comprises a corona discharge device for ionising analyte.

5. A mass spectrometer as claimed in claim 1, wherein said one or more solvents elute from the gas chromatography device prior to the elution of said one or more analytes.

6. A mass spectrometer as claimed in claim 1, wherein said one or more first settings and/or said one or more second settings are selected from the group consisting of: (i) a current or a corona current supplied to said atmospheric pressure ionisation ion source; (ii) a gas flow or a cone gas flow; (iii) an auxiliary gas flow; (iv) a voltage or a corona voltage applied to said atmospheric pressure ionisation ion source; (v) a polarity or a corona polarity of a voltage applied to said atmospheric pressure ionisation ion source; (vi) a temperature of one or more components of said atmospheric pressure ionisation ion source; (vii) a voltage offset, an ion source voltage offset or a cone voltage offset; and (viii) a makeup gas flow, a reference gas flow or a modifier gas flow.

7. A mass spectrometer as claimed in claim 6, wherein said control system is arranged and adapted to set said current or corona current at a first constant current value I1 during said first period of time and/or wherein said control system is arranged and adapted to set said current or corona current at a second constant current value I2 during said second period of time.

8. A mass spectrometer as claimed in claim 7, wherein said control system is arranged and adapted to set said first current value I1 or set said second current value I2 at a value selected from the group consisting of: (i) 0 µA; (ii)<1 µA; (iii) 1-2 µA; (iv) 2-3 µA; (v) 3-4 µA; (vi) 4-5 µA; (vii) 5-6 µA; (viii) 6-7 µA; (ix) 7-8 µA; (x) 8-9 µA; (xi) 9-10 µA; (xii) 10-11 µA; (xiii) 11-12 µA; (xiv) 12-13 µA; (xv) 13-14 µA; (xvi) 14-15 µA; (xvii) 15-16 µA; (xviii) 16-17 µA; (xix) 17-18 µA; (xx) 18-19 µA; (xxi) 19-20 µA; (xxii) 20-21 µA; (xxiii) 21-22 µA; (xxiv) 22-23 µA; (xxv) 23-24 µA; (xxvi) 24-25 µA; (xxvii) 25-26 µA; (xxviii) 26-27 µA; (xxix) 27-28 µA; (xxx) 28-29 µA; (xxxi) 29-30 µA; (xxxii) 30-40 µA; (xxxiii) 40-50 µA; and (xxxiv) >50 µA.

9. A mass spectrometer as claimed in claim 7, wherein I1<I2 or wherein I1>I2.

10. A mass spectrometer as claimed in claim 7, wherein said first constant current value I1 is different to said second constant current value I2.

11. A mass spectrometer as claimed in claim 10, wherein said first constant current value I1 is ten times as great as said second constant current value I2.

12. A mass spectrometer as claimed in claim 6, wherein said control system is arranged and adapted to vary said current or corona current as a function of time during said first period of time and/or wherein said control system is arranged and adapted to vary said current or corona current as a function of time during said second period of time.

13. A mass spectrometer as claimed in claim 6, wherein said control system is arranged and adapted to set said gas flow, cone gas flow, auxiliary gas flow, makeup gas flow, reference gas flow or modifier gas flow at a first constant gas flow value Q1 during said first time and/or wherein said control system is arranged and adapted to set said gas flow, cone gas flow, auxiliary gas flow, makeup gas flow, reference gas flow or modifier gas flow at a second constant gas flow value Q2 during said second time, wherein optionally said control system is arranged and adapted to set said first gas flow value Q1 and/or wherein said control system is arranged and adapted to set said second gas flow value Q2 at a value selected from the group consisting of: (i) 0 L/Hr; (ii) <10 L/Hr; (iii) 10-20 L/Hr; (iv) 20-30 L/Hr; (v) 30-40 L/Hr; (vi) 40-50 L/Hr; (vii) 50-60 L/Hr; (viii) 60-70 L/Hr; (ix) 70-80 L/Hr; (x) 80-90 L/Hr; (xi) 90-100 L/Hr; (xii) 100-150 L/Hr; (xiii) 150-200 L/Hr; (xiv) 200-250 L/Hr; (xv) 250-300 L/Hr; (xvi) 300-350 L/Hr; (xvii) 350-400 L/Hr; (xviii) 400-450 L/Hr; (xix) 450-500 L/Hr; and (xx) >500 L/Hr.

14. A mass spectrometer as claimed in claim 13, wherein Q1<Q2 or wherein Q1>Q2.

15. A mass spectrometer as claimed in claim 6, wherein said control system is arranged and adapted to vary said gas flow, cone gas flow, auxiliary gas flow, makeup gas flow, reference gas flow or modifier gas flow as a function of time during said first period of time and/or wherein said control system is arranged and adapted to vary said gas flow, cone gas flow, auxiliary gas flow, makeup gas flow, reference gas flow or modifier gas flow as a function of time during said second period of time.

16. A mass spectrometer as claimed in claim 1, wherein said control system is arranged and adapted to operate said atmospheric pressure ionisation ion source at said one or more first settings for said first period of time upon detecting said one or more background substances eluting from said gas chromatography separation device and/or upon detecting one or more changes in an operating condition or operating efficiency of said ion source.

17. A mass spectrometer as claimed in claim 1, wherein said atmospheric pressure ionisation ion source is not turned OFF during elution of the one or more solvents from said gas chromatography separation device during said solvent front.

18. A method of mass spectrometry comprising:
operating an atmospheric pressure ionisation source at one or more first settings for a first period of time whilst one or more solvents elute from a gas chromatography separation device during a solvent front free of analytes which is prior to the elution of one or more analytes from said gas chromatography separation device; and then
operating said atmospheric pressure ionisation source at one or more second different settings for a second subsequent period of time whilst said one or more analytes elute from said gas chromatography separation device.

* * * * *